(12) United States Patent
Harootian

(10) Patent No.: US 6,181,767 B1
(45) Date of Patent: Jan. 30, 2001

(54) INTEGRATED, SELF-ALIGNING X-RAY DETECTOR

(75) Inventor: Simon George Harootian, Worcester, MA (US)

(73) Assignee: Analogic Corporation, Peabody, MA (US)

( * ) Notice: Under 35 U.S.C. 154(b), the term of this patent shall be extended for 0 days.

(21) Appl. No.: 09/283,715

(22) Filed: Apr. 1, 1999

(51) Int. Cl.[7] .................................................. G01N 23/00

(52) U.S. Cl. ............................................. 378/19; 378/154

(58) Field of Search ........................... 375/19, 154, 98.8; 250/370.07, 370.11

(56) References Cited

U.S. PATENT DOCUMENTS

| 4,338,521 | 7/1982 | Shaw et al. | 250/366 |
|---|---|---|---|
| 4,429,227 | 1/1984 | DiBianca et al. | 250/367 |
| 5,357,553 | 10/1994 | Ferlic et al. | 378/154 |
| 5,487,098 | 1/1996 | Dobbs et al. | 378/19 |
| 5,991,357 | 11/1999 | Marcovici et al. | 378/19 |
| 6,091,795 | 7/2000 | Schafer et al. | 378/19 |

*Primary Examiner*—David P. Porta
(74) *Attorney, Agent, or Firm*—McDermott, Will & Emery

(57) ABSTRACT

An integrated, self-aligning x-ray detector assembly for a computed x-ray tomography system includes an alignment grid for aligning an array of scintillator crystals with a corresponding array of photodiodes. The grid includes extensions which engage with a plurality of anti-scatter plates so that the anti-scatter plates and the scintillator crystals are in a predetermined alignment.

10 Claims, 2 Drawing Sheets

INTEGRATED, SELF-ALIGNING X-RAY DETECTOR

TECHNICAL FIELD

The present invention relates to x-ray detector systems for computed tomography (CT) scanners.

BACKGROUND OF THE INVENTION

CT scanners of the third-generation type include an X-ray source and X-ray detector system secured respectively on diametrically opposite sides of an annular disk. The latter is rotatably mounted within a gantry support so that during a scan the disk rotates about a rotation axis while X-rays pass from the source through an object positioned within the opening of the disk to the detector system.

The detector system typically includes an array of detectors disposed along an arc of a circle having a center of curvature at a focal point from which radiation emanates from the X-ray source. The X-rays that are detected by a single detector at a measuring instant during a scan are partially attenuated by the mass of all objects in their path. The detectors sense this attenuation and generate a single intensity measurement as a function of the attenuation, and thus the density, of the mass in the x-ray path.

For accurate image reconstruction from x-ray density data, the positions of the rays, and thus of the detectors, must be precisely known. Further, since dense matter tends to scatter X-rays, it is important that any radiation that does not traverse a straight line from the source to each detector be excluded from the measurements by each such detector. To remove this scattered radiation, a series of very thin x-ray opaque anti-scatter plates is typically inserted between the detectors and the object being scanned, with the individual plates aligned so as to collimate the x-rays from the radiation source by allowing to pass to the detectors substantially only those x-rays traversing a straight, radial line between the source and each detector.

Unfortunately, the need for the anti-scatter plates creates additional difficulties because if they cast an X-ray "shadow" on a detector, they will interfere with its measurements, unless all of the anti-scatter plates shadow all of the detectors uniformly. The output of each shadowed detector will be not only reduced, but also modulated by any detectable relative movement of the source, anti-scatter plates and/or detectors.

The difficulty of meeting these requirements is evident. In order to provide the resolution expected of modem X-ray tomographic scanners, hundreds of detectors are required, with several detectors located within a single degree of the arc of the x-ray beam. This makes the width of a typical detector on the order of a millimeter. The width of a typical anti-scatter plate is about ten percent of the width of a detector. The spaces between adjacent detectors are scarcely larger than that. Thus, extremely accurate detector and anti-scatter plate location and alignment is required. To further compound the problem, the whole assembly is usually rotated around the scanned object at a rate of about 60 to 120 rpm, generating substantial varying forces and requiring rugged mounting techniques. With the introduction of two-dimensional detector arrays, tolerance stacking occurs in two dimensions instead of only one, and it is even more critical to provide highly accurate positioning of the detectors and the anti-scatter plates.

A difficulty with high-resolution detector subsystems is obtaining and maintaining the relatively tight alignment requirements of the detectors and anti-scatter plates with the x-ray beams from the radiation source. Tolerances are further strained by any temperature and vibrational changes in the relative alignment of the subsystems.

Attempts have been made to facilitate the accurate location and alignment of detectors and anti-scatter plates in tomography systems. For example, U.S. Pat. No. 5,487,098 to Dobbs et al., assigned to the assignee of the present invention, discloses preassembled modules for the detector and anti-scatter plate arrays. The detector and anti-scatter plate modules are each attached to a support structure or spine which is then attached to a rotating gantry of the tomography system. Each detector module must be aligned with a corresponding anti-scatter plate module, and each pair of modules must be aligned relative to the focal spot, in order to maximize receipt of radiation.

U.S. Pat. No. 4,338,521 to Shaw et al. discloses a modular detector array that includes two detachably assembled portions, one containing the detectors and the other containing the anti-scatter plates. The two portions of the array must be assembled together in order to establish their mutual alignment. The assembled module must then be aligned with the radiation source and then fixedly mounted to the tomography apparatus.

U.S. Pat. No. 4,429,227 to DiBianca et al. discloses a modular x-ray detector which comprises a pair of diodes in a diode support frame, a pair of scintillator bars, and a collimator plate with extensions for engaging with a corresponding extension of the diode support frame. The collimator plate includes a pocket on each side for accommodating a scintillator bar. Each collimator plate/diode pair is independently mounted in slots in a pair of ceramic sections which are mounted to respective end members of an arcuate housing.

The prior art does not teach the use of a fully integrated detector/anti-scatter plate assembly in which the detectors and anti-scatter plates are intrinsically aligned with one another. It would therefore be advantageous to provide an x-ray detector and anti-scatter plate assembly which is fully integrated so that all of the diodes, scintillator crystals and anti-scatter plates are self-aligned as they are assembled together.

SUMMARY OF THE INVENTION

According to the invention, there is provided an integrated, self-aligning x-ray detector assembly, comprising:

a support for the detector assembly;

a plurality of photodiodes arranged on the support in a predetermined array pattern;

a corresponding plurality of electrical connections between the photodiodes and a signal processor for transmitting electrical signals from the photodiodes to the signal processor;

an alignment grid disposed over the photodiode array and including an array of cells corresponding to the array of photodiodes;

a plurality of scintillator crystals arranged in the cells of the alignment grid so that each photodiode in the photodiode array is paired with a corresponding scintillator crystal; and a plurality of anti-scatter plates engaged with a portion of the alignment grid so that the anti-scatter plates are in a predetermined alignment with respect to the scintillator crystals.

In one embodiment, the photodiodes and scintillator crystals are arranged in a one-dimensional array. In another embodiment, they are arranged in a two-dimensional array.

In a preferred embodiment, the alignment grid includes extensions that extend from opposite ends of the alignment grid. In one embodiment the extensions are in the plane of the alignment grid. In an alternate embodiment, the extensions are transverse to the plane of the alignment grid.

The assembly can further include an extension extending transversely from the plane of the alignment grid between the ends of the alignment grid.

In one embodiment, the anti-scatter plates are aligned with the scintillator crystals. In another embodiment, they are aligned with the spaces between the scintillator crystals.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be made to the following detailed description taken in connection with the accompanying drawings, in which.

DETAILED DESCRIPTION OF THE DRAWINGS

Figure 1:
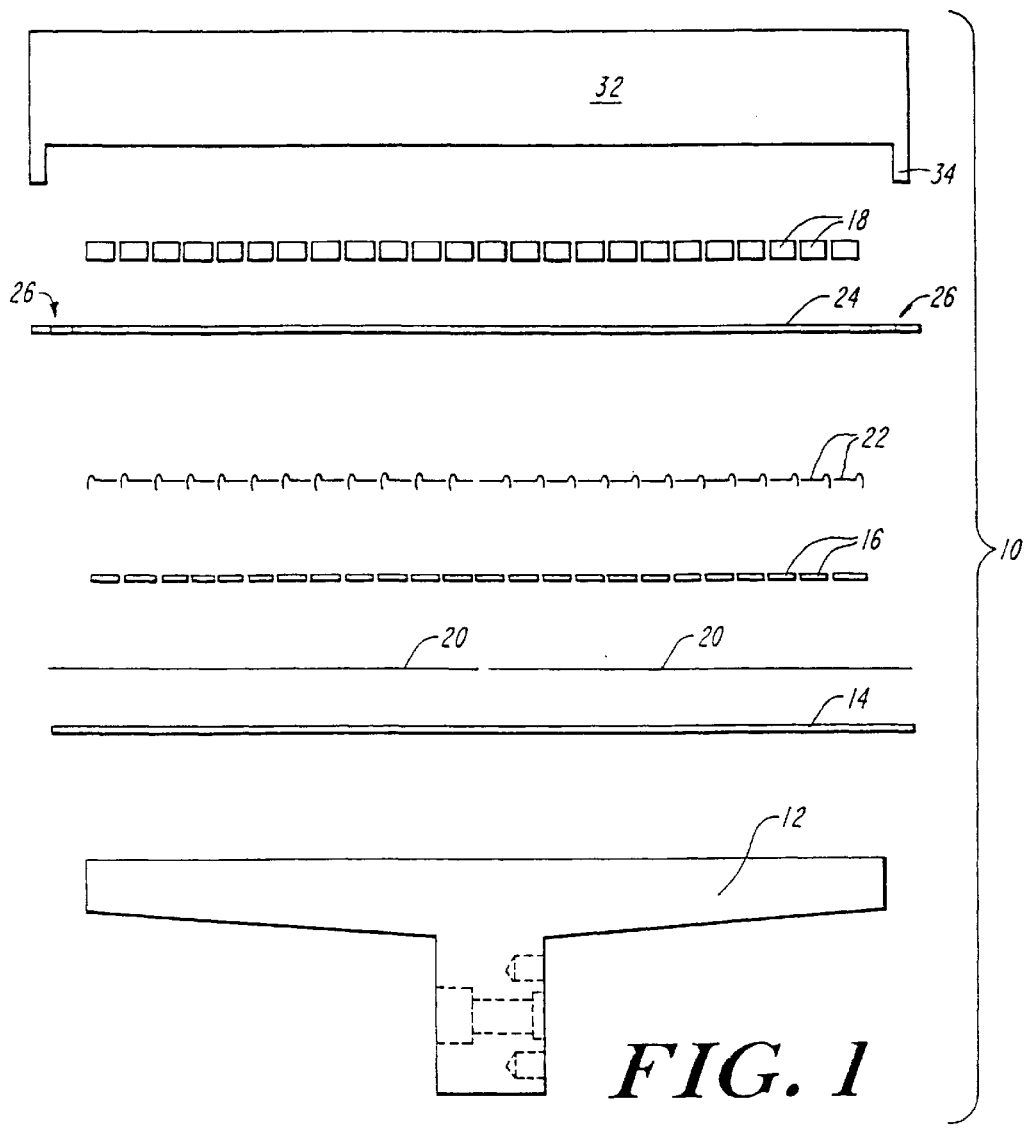
FIG. 1 is an exploded side view of an x-ray detector assembly according to the invention.

The detector assembly 10 of the present invention is shown in FIG. 1. A mounting block 12 supports a substrate 14 on which the photodiodes 16 and scintillator crystals 18 are disposed, as detailed more fully below. An electrically conductive interconnect pattern 20 is printed onto the substrate 14 and defines a network of electrical leads from the photodiodes 16 to a signal transmission cable (not shown). Photodiodes 16 are arranged in a predetermined array on the substrate so that each photodiode is electrically connected to the signal transmission cable via wire leads 22, which provide an electrical connection between the photodiode and the underlying printed interconnect network pattern 20.

Figure 2:
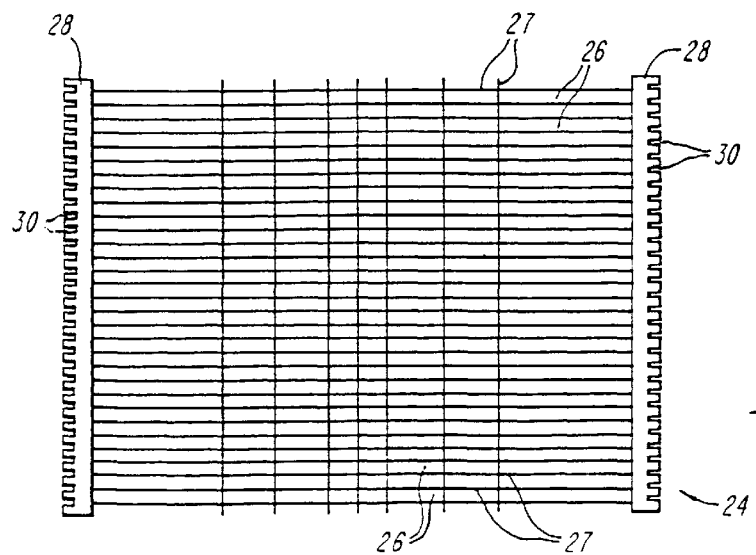
FIG. 2 is a plan view of one embodiment of an alignment grid used in the assembly of the invention.

Alignment grid 24 is illustrated in detail in FIG. 2. The grid 24 comprises an array of cells 26 separated by grid bars 27. The cells 26 are preferably dimensioned to accommodate one scintillator crystal 18 per cell.

The alignment grid 24 is disposed over the photodiode array so that each photodiode lies beneath a cell of the alignment grid. Scintillator crystals 18 are then placed over the grid and aligned within the respective cells of the grid, so that each scintillator crystal 18 is aligned with a corresponding photodiode 16.

As shown most clearly in FIG. 2, the alignment grid 24 includes a pair of extensions 28 which include slots 30. The slots are precisely dimensioned to receive an edge of an anti-scatter plate 32, as shown most clearly in FIGS. 3 and 4. The edges of the anti-scatter plates 32 fit into the slots 30 in the extensions 28 of the alignment grid 24 so as to be disposed over the scintillator crystal array in such a way as to prevent scattered x-rays from reaching the scintillator crystals. By the use of the alignment grid in this manner, the anti-scatter plates and the scintillator crystals are aligned precisely with respect to one another.

The alignment grid 24 is preferably made of a lightweight material, such as aluminum, which is accurately machined or etched to define the array of cells 26. In a preferred embodiment, the alignment grid is photo- or laser-etched to provide the necessary accuracy and precision in the spacing of the cells and the alignment of the slots with the cells and grid bars.

In one embodiment of the invention, the slots 30 in the alignment grid extensions are aligned with the grid bars 27 of the alignment grid. This alignment ensures that the anti-scatter plates 32 are positioned to cast a shadow over the grid bars 27, which define the spaces between adjacent scintillator crystals, and not over the crystals themselves. In another embodiment, the slots 30 are aligned with the cells 26 of the grid. This alignment ensures that the anti-scatter plates are positioned to cast a shadow over the scintillator crystals, preferably in a uniform manner so as to avoid modulation of the signal due to the presence of the anti-scatter plates over the crystals.

Figure 3:
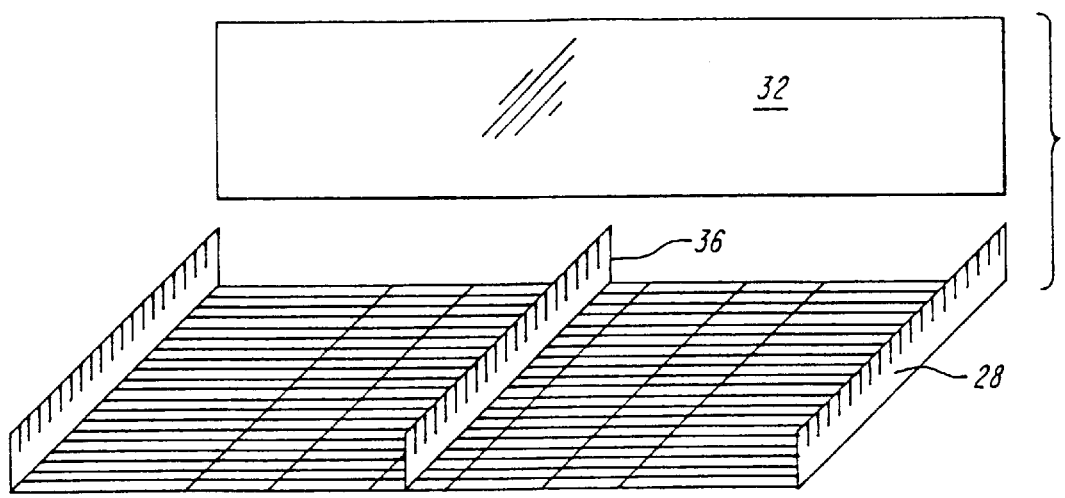
FIG. 3 is an exploded perspective view of another embodiment of an alignment grid assembled with anti-scatter plate.
Figure 4:
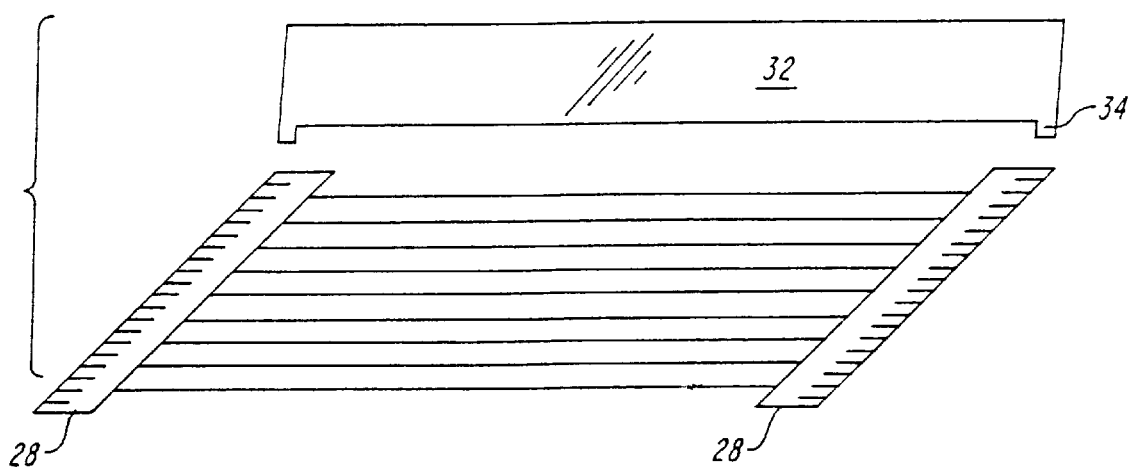
FIG. 4 is an exploded perspective view of still another embodiment of an alignment grid assembled with an anti-scatter plate.

The alignment grid is useful for self-alignment of anti-scatter plates with both one-dimensional crystal arrays, as indicated in FIG. 4, and two-dimensional arrays, as shown in FIG. 3. The scintillator crystals may be of different sizes, as indicated by the dimensions of the cells in the alignment grid shown in FIG. 2, or they may be of a uniform size, as indicated by the uniform cells of the grid shown in FIG. 4.

The extensions 28 of the alignment grid may be in the plane of the alignment grid, as shown in FIGS. 2 and 4, or transverse to the plane of the grid, as shown in FIG. 3. In the embodiment of FIG. 4, the anti-scatter plates 32 may include legs 34 or other extensions for facilitating engagement of the plates with the slots in the alignment grid extensions.

In the embodiment of FIG. 3, the extensions of the alignment grid extend transverse to the plane of the grid, and the anti-scatter plate may fit directly into the slots.

It is contemplated that the alignment grid shown in FIG. 3 may also include one or more additional extensions 36 disposed between the outside edges of the alignment grid and extending transverse to the plane of the alignment grid, to provide additional support and alignment for the anti-scatter plates 32, particularly in crystal arrays which are relatively long compared to their width.

Because certain changes may be made in the above apparatus without departing from the scope of the invention herein disclosed, it is intended that all matter contained in the above description or shown in the accompanying drawings shall be interpreted in an illustrative and not a limiting sense.

What is claimed is:

1. An integrated, self-aligning x-ray detector assembly, comprising:

a support for the detector assembly;

a plurality of photodiodes arranged on the support in a predetermined array pattern;

a corresponding plurality of electrical connections between said photodiodes and a signal processor for transmitting electrical signals from the photodiodes to the signal processor;

an alignment grid disposed over the photodiode array and including an array of cells corresponding to the array of photodiodes;

a plurality of scintillator crystals arranged in the cells of the alignment grid so that each photodiode in the photodiode array is paired with a corresponding scintillator crystal; and a plurality of anti-scatter plates engaged with a portion of the alignment grid so that the anti-scatter plates are in a predetermined alignment with respect to the scintillator crystals.

2. An integrated, self-aligning x-ray detector assembly according to claim 1, wherein the photodiodes and scintillator crystals are arranged in a one-dimensional array.

3. An integrated, self-aligning x-ray detector assembly according to claim 1, wherein the photodiodes and scintillator crystals are arranged in a two-dimensional array.

4. An integrated, self-aligning x-ray detector assembly according to claim 1, wherein the alignment grid includes extensions extending from opposite ends of the alignment grid.

5. An integrated, self-aligning x-ray detector assembly according to claim 4, wherein the extensions extend in a direction which is in the plane of the alignment grid.

6. An integrated, self-aligning x-ray detector assembly according to claim 4, wherein the extensions extend in a direction which is transverse to the plane of the alignment grid.

7. An integrated, self-aligning x-ray detector assembly according to claim 1, further comprising an extension extending transversely from the plane of the alignment grid from a location between the ends of the alignment grid.

8. An integrated, self-aligning x-ray detector assembly according to claim 1, wherein the anti-scatter plates are substantially aligned with the scintillator crystals.

9. An integrated, self-aligning x-ray detector assembly according to claim 1, wherein the anti-scatter plates are substantially aligned with the spaces between the scintillator crystals.

10. An x-ray detector assembly for a computed x-ray tomography system including a source of radiation, an x-ray detector assembly for detecting the radiation and for transmitting electrical signals representative of the detected radiation to a signal processor, and a support for an object to be scanned disposed between the source and the detector assembly, wherein the x-ray detector assembly comprises:

a support for the detector assembly;

a plurality of photodiodes arranged on the support in a predetermined array pattern;

a corresponding plurality of electrical connections between said photodiodes and a signal processor for transmitting electrical signals from the photodiodes to the signal processor;

an alignment grid disposed over the photodiode array and including an array of cells corresponding to the array of photodiodes;

a plurality of scintillator crystals arranged in the cells of the alignment grid so that each photodiode in the photodiode array is paired with a corresponding scintillator crystal; and a plurality of anti-scatter plates engaged with a portion of the alignment grid so that the anti-scatter plates are in a predetermined alignment with respect to the scintillator crystals.

* * * * *